United States Patent [19]

Armor

[11] Patent Number: 4,504,681
[45] Date of Patent: Mar. 12, 1985

[54] CATALYTIC OXIDATION OF PRIMARY AMINES TO OXIMES BY ELEMENTAL OXYGEN

[75] Inventor: John N. Armor, Hanover Township, Morris County, N.J.

[73] Assignee: Allied Corporation, Morris Township, Morris County, N.J.

[21] Appl. No.: 451,702

[22] Filed: Dec. 20, 1982

[51] Int. Cl.³ .................. C07C 131/04; C07C 131/00
[52] U.S. Cl. .................................... 564/267; 564/253; 564/268; 502/254; 502/305; 502/306; 502/323; 502/355
[58] Field of Search ............... 564/267, 268, 253, 262; 502/254, 305, 306, 323, 355

[56] References Cited

U.S. PATENT DOCUMENTS 2,706,204  4/1955  Kahr et al. ......................... 260/566
3,978,031  8/1976  Reginato et al. .................... 526/352
4,233,139  11/1980  Murrell et al. ...................... 502/305
4,337,358  6/1982  Armor ................................ 564/267

FOREIGN PATENT DOCUMENTS 47-25324  7/1972  Japan ................................ 260/126

OTHER PUBLICATIONS

N. Kalkert et al., German Chem. Eng. vol. 3, (1980), "Determination of Explosion Limits of Ammonia in Mixtures with Simple Hydrocarbons & Air" pp. 53-56.
W. L. Buckley et al., Chemical Eng. Prog. vol. 58, No. 2 pp. 81-84, (1962).
S. L. Teichner et al., Advances in Colloid and Interface Science, vol. 5, (1976), "Inorganic Oxide Aerogels" pp. 245-273.
F. A. Cotton and G. Wilkinson, 4th Ed. J. Wiley & Sons, pp. 850-854, "Advanced Inorganic Chemistry".

*Primary Examiner*—Natalie Trousof
*Assistant Examiner*—L. Hendriksen
*Attorney, Agent, or Firm*—Alan M. Doernberg; Thomas D. Hoffman; Richard C. Stewart, II

[57] ABSTRACT

A process for the production of oximes which comprises contacting, in the vapor phase, a primary saturated aliphatic or alicyclic amine of 2 to 12 carbon atoms with an elemental oxygen gas in the presence of an effective amount of a catalyst comprising an alumina or oxygen-containing tungsten substance on a metal oxide support using temperatures between about 130° and 230° C. at atmospheric pressure is disclosed. Preferred alumina catalysts are alumina xerogels, γ-alumina and acidic, fluorinated alumina. Preferred oxygen-containing tungsten catalysts are $WO_3$ on γ-alumina or $WO_3$ on alumina xerogels.

13 Claims, No Drawings 4,504,681

CATALYTIC OXIDATION OF PRIMARY AMINES TO OXIMES BY ELEMENTAL OXYGEN

BACKGROUND OF THE INVENTION

This invention relates to the conversion of primary saturated aliphatic and alicyclic amines having between 2 and 12 carbon atoms to oximes, comprising contacting said amine in a vapor phase with elemental oxygen and a catalyst comprising alumina or an oxygen-containing tungsten compound on a metal oxide support.

U.S. Pat. No. 4,337,358 (J. N. Armor) discloses a process for oxidizing primary saturated aliphatic and alicyclic amines by elemental oxygen to oximes, especially cyclohexylamine to cyclohexanone oxime, in the vapor phase using a silica gel catalyst and using temperatures of 120° C. to 250° C. and at atmospheric pressure.

Co-pending U.S. patent application Ser. No. 451,701 filed on an even date herewith and having co-inventors J. N. Armor, J. Yamanis, and E. J. Carlson discloses an improved catalyst comprising an oxygen-containing tungsten compound on alumina useful for production of oximes by selective oxidation, in the vapor phase, of saturated primary aliphatic and alicyclic amines such as cyclohexylamine with an elemental oxygen-containing gas; improved methods of preparation and regeneration of said improved catalyst are also disclosed.

A Japanese patent publication of July 11, 1972, having the No. SHO47-25324, relates to oxidation in liquid phase of primary aliphatic and alicyclic amines wherein a tertiary alcohol is present and preferably ammonia gas is present. A catalyst such as tungstic acid, phosphotungstic acid, molybdic acid, selenic acid, or selenious acid is preferably used. The highest conversions obtained in the examples are less than 20% and yields based on oxygen consumed are less than 50%.

U.S. Pat. No. 2,706,204 (K. Kahr) discloses that oximes are obtained by treating a primary amine, in the liquid phase, with hydrogen peroxide in the presence of a salt of an acid of tungsten, molybdenum or uranium as a catalyst.

SUMMARY OF THE INVENTION

The present invention provides a process for the conversion of primary saturated aliphatic and alicyclic amines, having between 2 and 12 carbon atoms in the molecule, to oximes, and comprises contacting said amine, in the vapor phase, with elemental oxygen and with essentially only unreactive diluent vapors or gases at amine and oxygen concentrations outside explosive limits in the presence of an effective amount of a catalyst comprising alumina or an oxygen-containing tungsten substance on a metal oxide support at a pressure between about 0.1 and 10 atmospheres (about 10 to about 1,000 kPa); and at a temperature between about 130° and 230° C. The term "unreactive diluent vapors or gases" as used herein means constituents of the vapor phase which do not adversely affect conversion of the amine function to oxime, when the other reaction conditions are made optimum. Such vapors or gases include, but are not limited to, so-called inert gases such as helium, nitrogen, and rare gases and also water vapor.

DETAILED DESCRIPTION

When "conversion" is referred to herein, it is defined as: 100×(mols of amine consumed)/(mols of amine fed into the reactor); "selectivity" is: 100×(mols of oxime produced)/(mols of amine consumed); and "yield" is: 100×(mols of oxime produced)/(mols of amine fed into the reactor).

Preferred temperatures for our process are generally in the range between 130° C. and 230° C.; and for conversion of cyclohexylamine to cyclohexanone oxime, which is the preferred reaction in accordance with this invention, preferred temperatures are between about 140° C. and 175° C. Such temperatures allow a reasonable conversion in a contact time of the heated gaseous reactants, at reaction temperature, with the catalyst generally in the range between about 0.05 and 5 minutes, depending on the reactivity of the particular amine and the temperature employed. For cyclohexylamine, preferred contact times are from about 3 to about 60 seconds, calculated on the basis that the reaction mixture approximates a perfect gas. The pressure used is conveniently about atmospheric but can be higher or lower if desired. The concentration by volume of the reactants are usually between about 0.5% and 6%, preferably about 3% amine and about 5%-30% oxygen, preferably about 11% oxygen. However, at 3% cyclohexylamine, there was little variation in selectivity to oxime as oxygen levels were varied from 3 to 30%.

The effective amount of a catalyst can be varied over a wide range depending upon the specific amine and catalyst as well as the reactor design chosen for the preferred cyclohexylamine. In the flow reactor described hereinbelow, the volume of the catalyst bed varies from 1 $cm^3$ to 4 $cm^3$ for a flow rate of reactants of about 10-20 $cm^3$/60 sec. For the preferred catalyst, $WO_3$ on $Al_2O_3$, the optimum catalyst bed was 2 $cm^3$ at a flow rate of cyclohexylamine and oxygen of about 20 $cm^3$/60 sec.

Amines to which our process is applicable are primary amines attached to primary or secondary carbons; including alicyclic amines, and especially cyclohexylamine; and also including ethylamine, n-propylamine, isopropylamine, n-butylamine, 2-aminobutane, 1-amino-3-methylbutane, 3-aminopentane, n-hexylamine, n-octylamine, laurylamine, aminocyclopentane, 1-amino-2-methylcyclohexane, 1-amino-2,6-dimethylcyclohexane, 1-amino-3,3,5,5-tetramethyl-cyclohexane, cyclopentylamine, cycloheptylamine, cyclooctylamine, cyclodecaamine, cyclododecaamine, diphenyl-methylamine and benzylamine.

Among the alumina-based catalysts and catalyst supports found useful in the selective oxidation of saturated primary aliphatic and alicyclic amines by oxygen are gamma alumina, [available from Girdler Chemical Co.]; fluorinated alumina ["KETJEN® NFF" fluorinated alumina (2.3 wgt % F−) as prepared and described in Example 1 of U.S. Pat. No. 3,978,031]; a heatactivated alumina-based aerogel obtained by heating at a temperature of at least about 400° C., in the presence of oxygen; an alumina-based aerogel prepared by venting a $C_1$-$C_5$ alcohol or mixture of same, under super-critical conditions from a mixture comprising a hydrolyzable aluminum compound, water and a $C_1$-$C_5$ alcohol; heatactivated alumina xerogels produced by heating an alumina aquagel, obtained by hydrolysis of hydrolyzable aluminum compounds, at a temperature of at least about 400° C., in the presence of elemental oxygen-containing gas such as air; and heat-activated alumina/silica xerogels produced by heating a mixture comprising alumina and silica aquagels obtained by hydrolysis of hydrolyzable aluminum and silica compounds, at a temperature of at least about 400° C., in the presence of an elemental oxygen-containing gas such as air.

Among the hydrolyzable aluminum compounds found useful for the preparation of alumina xerogels and aerogels are aluminum ($C_1$–$C_{10}$) alkoxides, preferably aluminum ($C_3$–$C_5$) sec-alkoxides and more preferably, aluminum isopropoxide and aluminum sec-butoxide.

Among the hydrolyzable silica compounds found useful in the preparation of alumina/silica xerogels are tetramethyl orthosilicate (TMOS), and tetraethyl orthosilicate. The preferred alumina-based catalysts are alumina xerogels, gamma alumina, acidic fluorinated alumina and alumina/silica xerogels. Oxygen-containing tungsten substances, preferably oxygen-containing tungsten(VI) substances, act as promoters for selected metal oxide catalysts such as alumina xerogels, gamma alumina, alumina-based aerogels, high surface area magnesium oxide and alumina/silica xerogels but surprisingly not for silicas such as those that are disclosed in U.S. Pat. No. 4,337,358 as catalysts for oxidation of primary saturated amines to oximes by elemental oxygen.

Among the oxygen-containing tungsten(VI) compounds found useful as promoters in the process of the present invention are tungsten(VI) oxide, $WO_3$, salts of tungstate, $WO_4^{-2}$, salts of isopolytungstates, such as paratungstate A, $HW_6O_{21}^{-5}$, paratungstate Z, $W_{12}O_{41}^{-10}$ and metatungstate, $W_{12}O_{39}^{-6}$, preferably ammonium metatungstate, tungstic acid, phosphotungstic acid, borotungstic acid and heteropolyanions containing tungsten(VI) such as are disclosed in "Advanced Inorganic Chemistry" by F. A. Cotton and G. Wilkinson, 4th Ed. J. Wiley & Sons, pp. 850–854.

Preferred oxygen-containing tungsten on metal oxide catalysts for the present process are formed by impregnating ammonium metatungstate, phosphotungstic or tungstic acid on a metal oxide support such as gamma alumina, acidic, fluorinated alumina, alumina xerogels, high surface area MgO, i.e., MgO having a surface area greater than 20 $m^2/g$ and alumina/silica xerogels, but not on α-alumina. A commercial material, 10% oxygen-containing tungsten substance on alumina, probably 10% $WO_3$ on gamma alumina available from Strem Chemical Co., was also found effective to convert 19% of cyclohexylamine into the oxime (selectivity was 61%).

The general procedure followed for the preparation of the oxygen-containing tungsten on a metal oxide catalyst was the well-known technique of "incipient wetness". The preferred $WO_3$ on an alumina xerogel was prepared by hydrolysis of the aluminum alkoxide to alumina aquagel and volatile alcohol in the presence of a water soluble tungsten(VI) compound, preferably ammonium metatungstate, followed by calcination in oxygen at a temperature of at least 400° C. for four hours to give $WO_3$ on an alumina xerogel.

For cyclohexylamine there was no substantial change in selectivity to oxime as the weight % of the oxygen-containing tungsten substance (basis W) on gamma alumina was varied from 3–20%.

The alumina-based and oxygen-containing tungsten substance on metal oxide catalysts useful in the process of the present invention have a surface area of between about 10 and about 800 $m^2/g$, preferably at least 60 to about 400 $m^2/g$ and more preferably about 100 to about 400 $m^2/g$. The average pore volumes preferably range from about 0.1 to about 9 cc/g. The best catalyst had a surface area between about 150 and about 400 $m^2/g$ and a pore volume of about 2 cc/g. With these best catalysts, best results were achieved with a cyclohexylamine concentration of between about 1% and about 4% by volume, an oxygen concentration of between about 3% and about 30% by volume, atmospheric pressure, a temperature between about 140° C. and 175° C. and a contact time of heated gaseous reactants with a catalyst between about 2 and 8 seconds. Neither temperature, pressure, feed ratios nor contact times appeared particularly critical to conversion and selectivity. Contact times of about 3 to about 60 secs were especially preferred for obtaining selectivities of greater than about 50% to oxime. Contact times outside of this especially preferred range are permissible but less preferred for operation of the present invention.

It is, however, desirable to operate with oxygen and amine volume proportions outside the explosive region. For most organics and air (i.e. about 20 volume percent oxygen), the explosive region at atmospheric pressure has a lower limit of 2–5% and an upper limit of 4–8%, varying among specific organics. Examples of this phenomena are well known in the literature, as evidenced by N. Kalkert et al., "Determination of Explosion Limits of Ammonia in Mixtures with Simple Hydrocarbons and Air", *German Chem. Eng.* Vol. 3, pp. 53–56 (1980); W. L. Buckley et al., *Chemical Eng. Prog.* Vol. 58, No. 2, pp. 81–84 (1962). Upper and lower limits for a particular organic amine, for a particular oxygen concentration, and a particular pressure can be estimated from the literature and determined more precisely by routine experimentation.

It is preferred to operate with an amine concentration lower than the lower limit of the explosive region. It is permissible, but less preferred to operate with more amine than the upper limit of the explosive region. The latter mode of operation has the disadvantages of requiring greater recycle and of entering the explosive region as reaction occurs, both disadvantages being less likely in the former mode of operation.

In the Examples below, the reaction was carried out in a borosilicate glass tube of about 14 mm outside diameter, containing a glass frit or a plug of quartz wool to hold the catalyst in place or in a stainless steel tube of 9.5 mm outside diameter, containing a stainless steel screen to hold the catalyst bed in place. The glass or stainless steel tube reactor, equipped for downward feed of the reactants in the gas phase in concurrent flow, was contained inside a tube furnace, electrically heated. As the catalyst is made deeper, under otherwise the same conditions, the extent of conversion increases. The depth of the catalyst bed can be varied; typically it can be about 1 to 2.5 cm in depth. The temperature, measured at the wall of the furnace, was varied from 130° to 230° C. The reactor can be operated manually and also automatically using a cam timer to actuate the sampling valves for reactants and products.

The amine was fed as vapor from a saturator. The products emerging from the bottom of the reactor passed through heated lines and could be diverted for analysis by gas chromatography.

EXAMPLE 1

Cyclohexylamine is vaporized by passing the gases (inert gas, conveniently helium) through a vaporizer maintained at a temperature, specifically 83° C., at which the cyclohexylamine vapor pressure provides 2% by volume of cyclohexylamine in the reaction gases. The oxygen percent was about 11% and the balance was helium gas. The flow rate of total vapors and gases at atmospheric temperature and pressure was about 20 cm³/min. The reactor was set up for downward flow of the gases through a bed of catalyst, which was specifically the 10% available as described by the manufacturer Strem Chemical Co. as having an average pore volume of 0.35 cc/g and BET surface area of 118 square meters per gram. The volume of the catalyst bed was 2 cm³; and the temperature employed was about 160° C. On the basis that the heated gaseous reaction mixture approximates a perfect gas, the contact time is calculated as about 6 seconds on a superficial basis.

The results obtained showed conversion of about 11.1% and selectivity of about 56%, i.e., a yield of about 6.2% per pass of the reaction mixture over the catalyst.

Generally, similar results can be obtained with other primary saturated aliphatic and alicyclic amines, having between two and 12 carbon atoms in the molecule, by adjusting the ratios of reactants, and adjusting the temperatures and contact times within the broad ranges above indicated (130°–230° C. and 3–60 seconds).

EXAMPLE 2

The oxidation of cyclohexylamine by oxygen was conducted over various aluminas in accordance with the procedure and apparatus of Example 1. The results are summarized in Table 1.

TABLE 1

Oxidation of CAM[a] to CONE Oxime[b] by $O_2$ in the Presence of Various Aluminas

| Run | Catalyst[c] | T (°C.) | Y[d] | C[e] | S[f] |
|---|---|---|---|---|---|
| 1 | $\gamma$-$Al_2O_3$[1] | 148 | 1.5 | 3.3 | TLC[g] |
| 2 | $\gamma$-$Al_2O_3$[1] | 161 | 4.2 | 8.5 | 50 |
| 3 | $\gamma$-$Al_2O_3$[1] | 192 | 3.9 | 18.2 | 22 |
| 4 | $\gamma$-$Al_2O_3$[1] | 227 | 3.4 | 42 | 8.3 |
| 5 | acidic, $F^-$/$Al_2O_3$[2] | 145 | 7 | 15 | 64 |
| 6 | acidic, $F^-$/$Al_2O_3$[2] | 155 | 5.8 | 11 | 53 |
| 7 | acidic, $F^-$/$Al_2O_3$[2] | 161 | 9 | 15 | 63 |
| 8 | acidic, $F^-$/$Al_2O_3$[2] | 163 | 6 | 15 | 39 |
| 9 | $\alpha$-$Al_2O_3$[3] | 170 | None | — | — |
| 10 | MgO[4] | 145–227 | None | <10 | — |
| 11 | $Al_2O_3$—$SiO_2$ aerogel[5] | 176 | 4.6 | 19 | 24 |

Footnotes to Table 1
[a]CAM is cyclohexylamine
[b]CONE oxime is cyclohexanone oxime
[c]11 mm diameter bed of catalyst; catalyst volume was 1 cm³ unless otherwise specified, 2–4% CAM 10–13% $O_2$; Total Flow Rate was 20–21 cpm (cm³/min)
[d]Yield of CONE oxime
[e]Conversion of CAM
[f]Selectivity to CONE oxime
[g]TLC: Too low to measure selectivity accurately
[1]gamma $Al_2O_3$ obtained from Girdler Chemical Co.; 3% CAM + 11% $O_2$; Total flow rate = 20 cpm; 1 g (volume Ca. 2 cm³) was used
[2]Acidic, fluorinated alumina ("KETJEN ® NFF") was prepared as described in Example 1 of U.S. Pat. No. 3,978,031 (fluoride concentration 2.3 wgt %)
[3]1 g (volume = 2 cm³) obtained from Girdler Chemical Co. was used; 3% CAM; 11% $O_2$; Flow Rate 20 cpm
[4]1 g (volume = 2 cm³) obtained from Harshaw Chemical Co. was used; SA = 11.8 m²/g 2.8% CAM; 13% $O_2$; Flow Rate = 21 cpm
[5]1 g (volume = 4 cm³) prepared from Al sec-butoxide + TMOS using a procedure described by S. J. Teichner et al. in the article entitled "Inorganic Oxide Aerogels" in Advances in Colloid and Interface Science, Volume 5, 1976 p. 245–273.

EXAMPLE 3

A variety of oxygen-containing tungsten substances were impregnated on gamma alumina by the well known technique of incipient wetness. A solution of the tungsten source, e.g., ammonium metatungatate (AMT), was slurried with gamma alumina and the slurry so formed was evaporated to dryness. The solid was recovered and heated in air at 400° C. for 1.5 hours. The results obtained by using these catalysts for oxidation of cyclohexylamine in accordance with the procedure and apparatus of Example 1 are summarized in Table 2.

TABLE 2

Oxidation of CAM[a] to CONE Oxime[b] by $O_2$ in the Presence of Various Tungsten Substances Impregnated on Gamma Alumina

| Run | Catalyst[f] | T (°C.) | Y[c] | C[d] | S[e] |
|---|---|---|---|---|---|
| 12 | $\gamma$-$Al_2O_3$[1] | 162 | 5.9 | 23 | 26 |
| 13 | 10% AMT/$\gamma$-$Al_2O_3$[2] | 162 | 15 | 25 | 61 |
| 14 | 10% $WO_3$/$\gamma$-$Al_2O_3$[3] | 161 | 11 | 19 | 61 |
| 15 | 10% PTA/$\gamma$-$Al_2O_3$[4] | 160 | 10 | 17 | 57 |
| 16 | 3% $WO_3$/$\gamma$-$Al_2O_3$[5] | 165 | 9.5 | 20 | 48 |
| 17 | 10% $WO_3$/$\gamma$-$Al_2O_3$[5] | 159 | 15 | 28 | 54 |
| 18 | 21% $WO_3$/$\gamma$-$Al_2O_3$[5] | 165 | 12 | 23 | 53 |
| 19 | pure $WO_3$[6] | — | 16 | 5 | 31 |

Footnotes to Table 2
[a]CAM = cyclohexylamine
[b]CONE Oxime = cyclohexamine oxime
[c]Y = yield of CONE Oxime
[d]C = conversion of CAM
[e]S = selectivity to CONE Oxime
[f]General Conditions 3% CAM; 11% $O_2$; Flow Rate 20 cpm; 11 mm diameter bed; 2 cm³ catalyst vol.
[1]Obtained from Girlder Chemical Co. and designated as T-126
[2]AMT = ammonium meta tungstate; 0.60 g AMT in 16 mL of $H_2O$ was slurried with 4 g of $\gamma$-$Al_2O_3$ (Girdler T-126), evaporated and solid dried in air at 125° C. for 3 hr.
[3]Commercial catalyst obtained from Alpha (Cat #11857); SA = 145 m²/g and believed to be $WO_3$ on $\gamma$-$Al_2O_3$.
[4]PTA = phosphotungstic acid; 0.60 g of PTA in 16 mL of $H_2O$ was slurried with 4.4 g of $\gamma$-$Al_2O_3$ (Girdler T-126).
[5]$WO_3$ = Tungstic acid; 10% $WO_3$/$\gamma$-$Al_2O_3$ was prepared by adding a solution of 0.60 g of $WO_3$ in 16 mL of $H_2$ $O$ containing 12 drops of conc. $NH_4OH$ to 4.4 g of $\gamma$-$Al_2O_3$ (Girdler T-126), evaporating the slurry so formed to dryness and heating solid in air at 125° C. for 3 hrs.
[6]"Catalytic $WO_3$" obtained from Strem Chemical Co., Cat #74-300; SA = Ca. 17 m²/g.

EXAMPLE 4

The use of ammonium metatungstate (AMT) on various metal oxide supports as a catalyst for the oxidation of cyclohexylamine by elemental oxygen was performed in accordance with the procedure and apparatus of Example 1. The catalysts were prepared by the incipient wetness technique by impregnating an aqueous solution of 0.63 g of AMT on 4.4 g of $\gamma$-$Al_2O_3$ 20–60 mesh (volume ca. 4.5 cm³), evaporating the slurry to a solid and drying the solid in air at 125°–220° C. before use. In runs 23–25 the % conversion of cyclohexylamine was low, i.e. 10–12%, and it was experimentally difficult to measure accurately the % selectivity to cyclohexanone oxime. In run #23, the % conversion was about 10% and the % selectivity, reported as >30% may have been as high as 70%. The results of oxidation of cyclohexylamine using the various catalysts are summarized in Table 3 below.

TABLE 3

Oxidation[a] of CAM[b] to CONE Oxime[c] by Oxygen in the Presence of 10% AMT[d] on a Variety of Metal Oxide Supports

| Run | 10% AMT on Solid Support | T (°C.) | Y[e] | C[f] | S[g] |
|---|---|---|---|---|---|
| 20 | $\gamma$-$Al_2O_3$[1] | 165 | 15 | 25 | 61 |
| 21 | $\alpha$-$Al_2O_3$[2] | 160 | None | <5 | 0 |
| 22 | acidic, $F^-$/$Al_2O_3$[3] | 165 | 12.9 | 23 | 55 |
| 23 | $Al_2O_3$ aerogel[4] | 165 | 7.3 | — | >30 |
| 24 | ASB[5]/$H_2O$ | 165 | 8 | 12 | 69 |
| 25 | MgO[6] | 165 | 2 | 10 | 19 |
| 26 | $SiO_2$/$Al_2O_3$[7] | 171 | 9 | 22 | 41 |
| 27 | TMOS/$NH_4OH$[8] | 165 | 6.5 | 20 | 33 |

TABLE 3-continued

Oxidation[a] of CAM[b] to CONE Oxime[c] by Oxygen in the Presence of 10% AMT[d] on a Variety of Metal Oxide Supports

| Run | 10% AMT on Solid Support | T (°C.) | Y[e] | C[f] | S[g] |
|-----|--------------------------|---------|------|------|------|
| 28  | Porasil A                | 165     | 4.8  | 15   | 32   |

Footnotes to Table 3
[a]General Conditions: 2% CAM; 10% O$_2$; Total Flow Rate 20 cpm; Diameter of catalyst bed: 11 mm; volume of catalyst 2 cm$^3$ at 20–60 mesh; All catalysts were dried in air at 125–220° C. prior to testing
[b]CAM = cyclohexylamine
[c]CONE Oxime = cyclohexanone oxime
[d]AMT = ammonium metatungstate, obtained from MCB, Technical grade
[e]Y = yield of CONE oxime
[f]C = conversion of CAM
[g]S = selectivity to CONE oxime
[1]gamma alumina (Girlder Chemical Co. T-126)
[2]alpha alumina (Girlder Chemical Co.)
[3]AMT (0.6 g) in 8 mL of H$_2$O was added to 4.4 g of acidic, fluorinated alumina ("KETJEN ® NFF") which was prepared as described in Example 1 of U.S. Pat. No. 3,978,031; (fluoride concentration in "KETJEN ® NFF" was 2.3 wgt %)
[4]The mixed oxide aerogel, alumina-WO$_3$ aerogel was prepared by adding a solution of 14.8 g (0.0599 mol) of Al(sec-butoxide)$_3$ (ASB) in 15 mL of isopropanol to an aqueous solution of 0.45 g (0.361 mol) of AMT in 6.5 mL of H$_2$O [2.01 times the stoichiometric amount of H$_2$O required to completely hydrolyze ASB to Al(OH)$_3$]. The % selectivity to oxime may have been as high as 70%. Methanol (100 mL) was added and the pasty mix so formed was stirred at 50° C. to form a fluid suspension which was charged to an autoclave. The autoclave was heated to 275° C. and solvents vented under supercritical conditions. The mixed oxide aerogel so formed was white; BET surface area: 706 m$^2$/g; pore volume (Hg) = 5.2 cm$^3$/g
[5]ASB = Al(sec-butoxide)$_3$. Mixed oxide xerogel (WO$_3$/Al$_2$O$_3$) was formed by dissolving 0.225 g of AMT in 3.25 mL of H$_2$O with 7.4 g of ASB. The slurry was evaporated to dryness and solid heated in air at 400° C. for 5 hours.
[6]Prepared by adding 4.4 g of MgO to 0.6 g of AMT in 8 mL of H$_2$O.
[7]Prepared by adding 0.14 g of AMT in 5 mL of H$_2$O to 1.0 g (4.5 cm$^3$) of SiO$_2$/Al$_2$O$_3$ gel.
[8]Prepared by adding 0.35 g of AMT in 1.5 mL of 5N NH$_4$OH to 6.1 g of TMOS in 4 mL of methanol.
[9]Prepared by adding 1.0 g of AMT in 20 mL of H$_2$O to 7.0 g (15 cm$^3$) of Porasil A (Waters Associates)
The comparison of results of runs #27 and 28 shows the presence of NH$_4$OH is not critical.

EXAMPLE 5

The following example is illustrative of the best mode of preparation of catalyst comprising an oxygen containing tungsten (VI) substance on an alumina xerogel support now contemplated by the inventor. This preparation is the invention of J. N. Armor, E. J. Carlson and J. Yamanis and is disclosed in U.S. patent application, Ser. No. 451,701, filed on an even date herewith.

There was placed in a flat-bottomed "Pyrex" dish 10.0 g (0.0405 mol) of aluminum sec-butoxide, a viscous and moisture-sensitive liquid. A solution of 0.31 g ammonium metatungstate (AMT, 85% WO$_3$) dissolved in 5 cc water (0.278 mol) was promptly added with manual stirring. Hydrolysis and solidification of this alkoxide to a granular mass of alumina occurred in a matter of seconds. The temperature of the mass rose to 70°–75° C. as stirring was continued. The wet material was aged at ambient conditions for one to two hours and then dried overnight at 100°–125° C. to remove the butanol coproduct, excess moisture, and any other volatiles. In the same dish, the dried material was heated to 400° C. in a muffle furnace for about four hours during which period the alumina and the tungstate were further dehydrated. Remaining was a white, or nearly white, granular material of low bulk density of about 0.20 g/cc. The quantities of starting materials were calculated to give 10 parts tungsten per 100 parts dry alumina, equivalent to 12.6 parts WO$_3$ per 100 parts dry alumina. Surface properties of the final product varied with the amount of water applied in the hydrolysis step. A ratio of 5 cc water per 10 g ASB was found optimum for catalyst performance in U.S. patent application Ser. No. 451,701. The addition of lower alcohol diluents to the hydrolysis step did not appear beneficial from a performance standpoint. The results of oxidation of cyclohexylamine by oxygen, (performed in accordance with the apparatus and procedure of Example 1) with the catalyst of this Example is reported in Table 4, Run #31.

TABLE 4

Comparative Examples

| Run | Catalyst[a] | T (°C.) | Y[b] | C[c] | S[d] |
|-----|-------------|---------|------|------|------|
| 30 | Al$_2$O$_3$[1] | 160 | 7.7 | 27 | 28 |
| 31 | 10% WO$_3$/Al$_2$O$_3$[2] | 160 | 21 | 33 | 64 |
| 32 | Al$_2$O$_3$/SiO$_2$[3] | 155 | None | — | — |
| 33 | Al$_2$O$_3$/SiO$_2$[3] | 185 | 4 | 32 | 13 |
| 34 | 10% WO$_3$/Al$_2$O$_3$—SiO$_2$[4] | 173 | 6.8 | 15.7 | 43 |
| 35 | MgO[5] | 145–227 | None | — | — |
| 36 | WO$_3$/MgO[6] | 165 | 2 | 10 | 19 |
| 37 | γ-Al$_2$O$_3$[7] | 161 | 4.2 | 23 | 26 |
| 38 | γ-Al$_2$O$_3$[7] | 161 | — | 8.5 | 50 |
| 39 | 10% WO$_3$/γ-Al$_2$O$_3$[8] | 161 | 11 | 19 | 61 |
| 40 | Porasil A[9] | 155 | 8 | 15 | 53 |
| 41 | 10% WO$_3$/Porasil A[10] | 159 | 15 | 28 | 54 |

Footnotes to Table 4
[1]1.0 g of Al$_2$O$_3$ xerogel formed from reaction of 5 g Al (sec-butoxide)$_3$ + 5 mL H$_2$O; calcined (O$_2$) at 400° C.; 2.8% CAM + 11% O$_2$; Total flow rate, 20
[2]1 g of xerogel catalyst formed from reaction of 0.31 g of ammonium metatungstate + 10 g of Al(sec-butoxide)$_3$ + 5 mL of H$_2$O, calcined in O$_2$ at 400° C; 2.8% CAM + 11% O$_2$; total flow rate 20 cpm
[3]Xerogel formed from reaction of 15.25 g of Al(sec-butoxide)$_3$ + 24 g of TMOS + 10.7 mL of H$_2$O; calcined in O$_2$ at 400° C.
[4]Prepared as described in Table 3 Run #26
[5]Support prepared as described in Table 1, Run #10
[6]Prepared as described in Table 3, Run #25
[7]Gamma alumina (Girlder Chemical Co., T-126)
[8]Commercial material obtained from Alpha
[9]Porasil A - a high purity SiO$_2$-gel obtained from Waters Associates, Mass.
[10]Prepared as described in Table 3, Run #28
[a]11 mm diameter catalyst bed; 2–3% CAM; 10–11% O$_2$; catalyst volume was 1–2 cm$^3$; Total flow Rate was 20–21 cpm;
[b]Y = Yield of CONE oxime;
[c]C = conversion of CAM;
[d]S = selectivity to CONE oxime

What is claimed is:

1. A process for the production of oximes which comprises contacting, in the vapor phase, a primary saturated aliphatic or alicyclic amine of 2 to 12 carbon atoms with an elemental oxygen gas in the presence of an effective amount of a catalyst comprising an oxygen-containing tungsten substance on a metal oxide support or alumina at a contact time of the heated gaseous reactants with the catalyst of between about 0.05 and 5 minutes.

2. The process of claim 1 wherein the catalyst comprises an alumina selected from a group consisting of gamma alumina, fluorinated alumina and a heat-activated alumina xerogel prepared by heating an alumina aquagel obtained by hydrolysis of a hydrolyzable aluminum compound, at a temperature of at least about 125° to about 400° C. in the presence of oxygen.

3. The process of claim 1 wherein the catalyst comprises fluorinated alumina.

4. The process of claim 1 wherein the aliphatic or alicyclic primary amine is cyclohexylamine.

5. The process of claim 1 wherein the catalyst comprises an oxygen-containing tungsten substance on a metal oxide support selected from a group consisting of alumina, MgO, heat-activated alumina aerogel, Al$_2$O$_3$/SiO$_2$ and a heat-activated alumina aquagel obtained by hydrolysis of a hydrolyzable aluminum compound, at a temperature of at least about 400° C.

6. The process of claim 5 wherein the oxygen-containing tungsten compound is an oxygen-containing tungsten(VI) compound.

7. The process of claim 6 wherein the oxygen-containing tungsten(VI) compound is tungsten(VI) oxide (WO$_3$), a salt of tungstate (WO$_4{}^{-2}$), a salt of isopolytungstate, tungstic acid, phosphotungstic acid or a heteropolyanious containing tungsten(VI).

8. The process of claim 6 wherein the catalyst is $WO_3$ supported on gamma alumina.

9. The process of claim 6 wherein the catalyst is $WO_3$ supported on fluorinated alumina.

10. The process of claim 6 wherein the catalyst is $WO_3$ supported on a heat-activated alumina obtained by heating, at a temperature of at least about 400° C. and in the presence of oxygen, an alumina aquagel containing an oxygen-containing tungsten(VI) compound prepared by hydrolysis of a hydrolyzable aluminum compound in the presence of an oxygen-containing tungsten(VI) compound.

11. The process of claim 9 wherein the hydrolyzable aluminum compound is aluminum sec-butoxide and the oxygen-containing tungsten compound is ammonium metatungstate.

12. The process of claim 5 wherein the reaction temperature of the vapor phase oxidation is between about 130° C. and 230° C.

13. The process of claim 11 wherein the reaction temperature is between about 140° C. and 175° C.

* * * * *